United States Patent [19]

Kawanishi et al.

[11] Patent Number: 5,215,712
[45] Date of Patent: Jun. 1, 1993

[54] APPARATUS FOR DETERMINATION OF ION CONCENTRATION, SPECIFIC GRAVITY, OR OSMOTIC PRESSURE OF SOLUTION

[75] Inventors: Tetsuro Kawanishi; Nobuko Suzuki; Hiroshi Suzuki, all of Ashigarakami, Japan

[73] Assignee: Terumo Kabushiki Kaisha, Tokyo, Japan

[21] Appl. No.: 582,167

[22] Filed: Sep. 14, 1990

[30] Foreign Application Priority Data

Sep. 14, 1989 [JP] Japan .................................. 1-236923
Sep. 14, 1989 [JP] Japan .................................. 1-236924

[51] Int. Cl.$^5$ ........................ G01N 9/36; G01N 31/04
[52] U.S. Cl. ........................................ 422/56; 422/57;
   422/82.09; 436/2; 436/169; 427/2
[58] Field of Search .................... 422/56, 57, 82.09;
   436/2, 169, 170; 427/2; 73/32 R

[56] References Cited

U.S. PATENT DOCUMENTS

| | | | |
|---|---|---|---|
| 3,992,158 | 11/1976 | Przybylowicz et al. | 23/253 |
| 4,015,462 | 4/1977 | Greyson et al. | 73/32 R |
| 4,038,485 | 7/1977 | Johnston et al. | 23/230 B |
| 4,108,727 | 8/1978 | Stiso et al. | 195/103.5 R |
| 4,318,709 | 3/1982 | Falb et al. | 23/230 R |
| 4,356,149 | 10/1982 | Kitajima et al. | 422/56 |
| 4,472,498 | 9/1984 | Masuda et al. | 435/7 |
| 4,532,216 | 7/1985 | Wang et al. | 436/2 |
| 4,965,047 | 10/1990 | Hammond | 422/58 |
| 5,064,615 | 11/1991 | Mangold et al. | 422/56 |

FOREIGN PATENT DOCUMENTS

| | | |
|---|---|---|
| 59285/80 | 2/1981 | Australia . |
| 77601/81 | 5/1982 | Australia . |
| 81982/82 | 10/1982 | Australia . |
| 0114403 | 1/1984 | European Pat. Off. . |
| 0349843 | 10/1990 | European Pat. Off. . |
| 62-95462 | 5/1987 | Japan . |

OTHER PUBLICATIONS

Patent Abstracts of Japan, vol. 011, No. 303 (P-622), Oct. 3, 1987.

Primary Examiner—James C. Housel
Assistant Examiner—David Redding
Attorney, Agent, or Firm—Burns, Doane, Swecker & Mathis

[57] ABSTRACT

A method for the determination of the ion concentration, specific gravity, or osmotic pressure of a solution, which comprises causing to contact a solution under test a coloring substance formed of a pigment or a precursor of pigment having solubility correlated with the ion concentration of said solution and detecting the solubility of said coloring substance in said solution, and an apparatus therefor.

21 Claims, 6 Drawing Sheets

APPARATUS FOR DETERMINATION OF ION CONCENTRATION, SPECIFIC GRAVITY, OR OSMOTIC PRESSURE OF SOLUTION

BACKGROUND OF THE INVENTION

1. Field of the Invention

This invention relates to a method for a determination of an ion concentration, specific gravity, or osmotic pressure of a solution and to an apparatus for use in the determination.

2. Description of the Prior Art

The determination of the specific gravity of a solution is widely practiced in the field of food industry, fermentation industry, or clinical test. In the field of clinical test, for example, the diagnosis of a renal disease by the determination of the specific gravity of a given patient's urine is in vogue. The specific gravity of urine represents the amount of a solute present in the urine and constitutes itself a useful barometer of the renal function. It is known that the magnitude of this specific gravity shows a satisfactory correlation with the ion concentration and osmotic pressure of urine. Generally, the specific gravity of urine from a healthy man falls in the range of 1.016 to 1.022. A specific gravity smaller than the lower limit of this range is a good reason for suspecting diabetes insipidus, acute renal failure, myelitis, etc. Conversely, a specific gravity larger than the upper limit of the range offers a convincing reason for suspecting nephrotic syndrome, various forms of abnormal loss of water, etc. Heretofore, it has been customary to determine the specific gravity of urine by the use of a pycnometer or a hydrometer or by the use of a urine refractometer or an osmometer which has a correlative bearing upon urine specific gravity.

The method which attains the determination with a pycrometer or a hydrometer, for example, however has been variously problematic as in respect that it necessitates an expensive measuring instrument, that it inevitably requires the measuring instrument to be sparingly susceptable to breakage, and that it suffers the measuring instrument to involve a complicated procedure. In the measures heretofore proposed for the solution of this problem, (A) a composition for the determination of specific gravity or osmolality of a given sample liquid, which composition comprises a substance capable of producing a discernible response as the function of the specific gravity or osmolality of the liquid and at least an effective number of microcapsules having the aforementioned substance hermetically contained therein and possessing a wall of a polymeric membrane translucent and susceptible of fracture under the pressure due to permeation and, therefore, operates by causing the contained substance to be released through the wall of membrane on the occurrence of a prescribed osmotic pressure gradient through the interior and exterior of the microcapsules and allowing the released substance to produce the discernible response and a measuring instrument formed by the use of the composition [JP-B-60-46,374(1985)], (B) a composition for the determination of the ionic strength of a liquid sample, which composition comprises a weakly acidic or weakly basic polyvalent macromolecular electrolyte and a pH supporting substance capable of inducing a discernible response during the course of ion exchange between the electrolyte and the liquid sample [JP-B-62-12,858(1987)], and (C) a device for testing a sample aqueous solution for specific gravity, which comprises a wettable substance exhibiting a capacity for absorption corresponding to the ion strength of the aqueous solution, a test layer containing an absorption indicating substance exhibiting solubility corresponding to the magnitude of variation in the capacity for absorption and consequently producing a change in transparency, and a supporting member serving as an optical background for the test layer [JP-A-62-95,462(1987)] have been renowed.

The methods using the compositions of (A), (B), and (C), however, invariably entail the disadvantage that the determination turns out to be expensive, complicated operationally, and deficient in accuracy.

As object of this invention, therefore, is to provide a novel method for the determination of the ion concentration, specific gravity, or osmotic pressure of a solution and an apparatus to be used in the determination.

SUMMARY OF THE INVENTION

The object described above is accomplished by a method for a determination of an ion concentration, specific gravity, or osmotic pressure of a solution, which comprises causing to contact a solution under test a coloring substance formed of a pigment or a precursor of pigment having resolubility correlated with the ion concentration the solution and detecting the solubility of the coloring substance in the solution.

This invention discloses a method for a determination mentioned above, wherein the coloring substance is a pigment possessing an ionically functional group. This invention also discloses a method for the determination mentioned above, wherein the detection of the solubility of the coloring substance formed of the pigment is accomplished by the determination of the absorbance of the solution. This invention also discloses a method for the determination mentioned above, wherein the detection of the solubility of the coloring substance formed of the precursor of pigment is accomplished by adding a developer to the solution thereby causing a coloring reaction of the solution and determining the absorbance of the solution resulting from the coloring reaction. This invention also discloses a method for the determination mentioned above, wherein the coloring substance formed of the precursor of pigment is a phenol compound or an aniline compound and the developer is an oxidation condensation coloring type compound or a diazo coupling type compound. This invention also discloses a method for the determination mentioned above, wherein the determination is carried out in the presence of a salt of a prescribed concentration added in advance for the adjustment of the range of ion concentration subjected to determination.

The object described above is further accomplished by an apparatus for the determination of the ion concentration, specific gravity, or osmotic pressure of a solution, which comprises a reagent layer having carried thereon a pigment having solubility correlated with the ion concentration in the solution and a spreading layer disposed contiguously to the reagent layer and adapting the two layers to allow the amount of the pigment dissolved out of the reagent layer into the spreading layer to be varied proportionately to the ion concentration of the solution under test and enable the ion concentration to be reflected in the density of color developed on the surface of the spreading layer.

This invention discloses an apparatus for a determination mentioned above, wherein the pigment is a water-soluble pigment possessing an ionically functional group. This invention also discloses an apparatus for the determination mentioned above, wherein the reagent layer comprises a water-permeable carrier and a pigment deposited thereon. This invention also discloses an apparatus for the determination mentioned above, wherein the carrier is a filter paper or a cloth. This invention also discloses an apparatus for the determination mentioned above, wherein the reagent layer is formed by having adsorptively dispersed in conjunction with a polymeric material on a carrier a pigment per se or a pigment adsorbed on minute particles. This invention also discloses an apparatus for the determination mentioned above, wherein the polymeric material is at least one member selected from the group consisting of polyvinyl pyrrolidone, polyvinyl alcohol, hydroxypropyl cellulose, and gelatin. This invention also discloses an apparatus for the determination mentioned above, wherein the minute particles are those of at least one member selected from the group consisting of sellaite, silica gel, polyamide, and alumina. This invention also discloses an apparatus for the determination mentioned above, wherein the spreading layer is a filter paper or a cloth. This invention also discloses an apparatus for the determination mentioned above, wherein the spreading layer incorporates therein a surfactant or a wetting agent. This invention also discloses an apparatus for the determination mentioned above, wherein the spreading layer contains a stated amount of a salt to be used for the adjustment of the range of ion concentration subjected to determination. This invention also discloses an apparatus for the determination of the ion concentration, specific gravity, or osmotic pressure of a solution, wherein the device for testing described above is carried on a supporting member.

Since the method for determination and the apparatus therefor according with the present invention are constructed as described above, they are capable of determining the ion concentration, specific gravity, or osmotic pressure of a solution accurately by a simple procedure without necessitating the expensive apparatus which has been indispensible to the conventional method.

Further, since the coloring substance to be used is a pigment or a precursor of pigment, the detection of ion concentration can be effected very easily by the determination of absorbance, the colorimetry, etc. Thus, the determination of ion concentration or specific gravity of varying solutions or body fluids such as urine can be effected easily.

EXPLANATION OF THE PREFERRED EMBODIMENT

In accordance with the present invention, the ion concentration of a given solution is determined by adding to the solution a coloring substance formed of a pigment or a precursor of pigment and measuring the amount of the coloring substance dissolved in the solution, the determination of the specific gravity of the solution is attained owing to the fact that this ion concentration is correlated with the specific gravity, and the osmotic pressure of the solution is attained owing to the fact that the osmotic pressure is proportional to the number of particles of a solute in a prescribed amount of solvent and, therefore, is correlated with the number of ions in the solution of an electrolyte, namely to the ion concentration of the solution.

As the coloring substance, any of pigments and precursors of pigment can be used on the condition that it should possess solubility correlated with the ion concentration. Specifically, for the coloring substance, it is an essential requirement that the solubility thereof should be variable with the ion concentration of the solution. The coloring substance formed of a pigment or a precursor of pigment having solubility correlated with the ion concentration in a solution generally possesses an ionically functional group and assumes a form countered with a counter ion. Indigo carmine, for example, has a sulfonic acid group as an ionically functional group and is countered with sodium ion.

The pigments which are effectively usable in the present invention include indigo carmine, basic blue 3, basic red 9, basic red 29, acid blue 120, acid red 11, acid red 97, crystal violet, brilliant blue G, naphthol green G, and procion blue HB, for example.

When a water-soluble precursor of pigment is used as a coloring substance, since this coloring substance per se is incapable of assuming color, it must be caused to produce color by the addition of a developer prior to the detection of solubility. The precursors of pigment usable effectively as the coloring substance herein include (1) phenol compounds such as phenol, resorcinol, pyrocatechol, salicylic acid, m-, p-hydroxysalicylic acids, o-, p-chlorophenols, o-, p-bromophenols, and fluoroglycinol and (2) aniline compounds such as aniline, N,N-dimethyl aniline, N,N'-diethyl aniline, N-sulfopropyl aniline, N-methyl-N-sulfopropyl aniline, N-ethyl-N-sulfopropyl aniline, N-ethyl-n-sulfopropyl toluidine, N-methyl-N-sulfopropyl hydroxy aniline, and N-ethyl-N-sulfopropyl hydroxy aniline, for example. The developers which are effectively usable herein include (A) oxidation condensation coloring type compounds such as 4-amino antipyrin and 3-methyl-2-benzothiazolinone (which requires an oxidizing agent such as, for example, potassium ferricyan during the reaction for coloration) and (B) diazo coupling type compounds such as fast red B salt, fast red AL salt, fast red ITR salt, fast red violet LB salt, fast violet B salt, fast blue B salt, fast blue BB salt, and fast blue RR salt, for example. Either of the developers of (A) and (B) can be used in any of the precursors of pigment of (1) and (2).

The coloring substance described above is preferably used in an amount just corresponding to or slightly in excess of the saturated concentration relative to the solution subjected to the determination.

When the coloring substance of the nature described above is brought into contact with the solution under test, the following ionic equilibrium is formed between the insolubles and the solubles.

$$P-A^+B^- \rightleftarrows P-A^+ + B^- \quad (I)$$

$$P-B^-A^+ \rightleftarrows P-B^- + A^+ \quad (II)$$

The equilibrium of the formula of (I) occurs when the coloring substance is basic and that of the formula of (II) occurs when the coloring substance is acidic.

When the ion concentration in the solution is high, the dissociation equilibrium tends to the left, namely in the direction of avoiding ionization. Conversely, when the ion concentration in the solution is low, the dissociation equilibrium tends to the right, namely in the direction of facilitating ionization. Thus, the ease with which the pigment dissolves in the solution increases in proportion as the ion concentration decreases. Conversely, the difficulty with which the pigment dissolves in the solution increases in proportion as the ion concentration increases.

The discernment of the ion concentration in the solution by virtue of the correlation between the ion concentration of the solution and the solubility thereof is accomplished by adding a coloring substance in an amount exceeding saturated concentration and then detecting either the amount of a dissolved portion of the coloring substance or the amount of an undissolved portion thereof. When a pigment is used as the coloring substance, for example, the discernment is carried out by adding the pigment in an amount exceeding the saturated concentration and then detecting the amount of a dissolved portion of the pigment or the amount of an undissolved portion of the pigment.

Various methods are available for the detection of the amount of a dissolved portion of the pigment. For example, this detection is accomplished by determining the absorbance of the supernatant of the solution containing no dissolved pigment. In this case, since the solution generally contains the pigment in a concentration closely approximating saturation, it cannot be used safely in its unmodified form as a sample for the determination of absorbance. The supernatant of the solution allows this determination when the supernatant is diluted to a concentration fit for determination or when the determination is carried out by the use of a cell having a very short light path. When a precursor of pigment is used as the coloring substance, the discernment of the amount of a dissolved portion of the precursor of pigment is preferably attained by a method which comprises taking a portion of the solution, causing this portion to assume a color by a reaction with a developer, and then determining the absorbance of the colored solution.

The method described above can be applied to ordinary analysis when it is performed with a testing device formed by having a prescribed amount of a pigment in advance in a test tube, for example. In this case, the analysis is accomplished by adding a prescribed amount of a solution subjected to the determination in the test tube, stirring the solution therein, taking out a part of the stirred solution, diluting the removed solution with distilled water, and then measuring the absorbance of the diluted solution.

Since this absorbance, as demonstrated in the working examples to be cited hereinafter, is correlated with the concentration and specific gravity of the solution, the determination of this absorbance consequently allows determination of the concentration and specific gravity. Further, since this absorbance is correlated with the ion concentration and, consequently, with the osmotic pressure, the determination of this absorbance allows determination of the osmotic pressure. Optionally, the detection may be carried out by colorimetry. The testing device, when necessary, may be prepared in the form of a urine-testing paper and used for the determination which is effected by measuring the intensity of reflected light.

The apparatus for determination according with the present invention basically comprises a reagent layer having deposited thereon a pigment having solubility correlated with the ion concentration in a solution and a spreading layer disposed contiguously to the reagent layer. The pigment in the reagent layer dissolves out of the reagent layer into the spreading layer in an amount varied proportionately to the ion concentration of the solution under test. The amount of the pigment so dissolved out is reflected in the density of the color assumed by the surface of the spreading layer. Since the osmotic pressure is directly proportional to the number of particles of solute in a prescribed amount of solvent, it is correlated with the number of ions in the solution of eletrolyte, namely, the ion concentration. Thus, the osmotic pressure is determined on the basis of this correlation.

As the pigment for this invention, any of water-soluble pigments can be used on the condition that it should possess solubility correlated with the ion concentration. Specifically, for this pigment, it is an essential requirement that the solubility thereof should be varied by the ion concentration of the solution. The pigment whose solubility is correlated with the ion concentration in the solution generally possesses an ionically functional group and assumes a form countered with a counter ion. Indigo carmine, for example, possesses a sulfonic acid group as an ionically functional group and assumes a form countered with sodium ion. The pigments which are effectively usable herein are as already enumerated.

Figure 1:
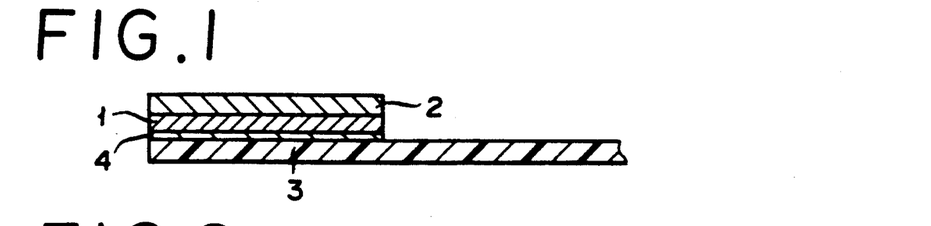
FIGS. 1 to 3 are cross sections illustrating various apparatuses for determination, each embodying the present invention.

Now, the present invention will be described below with reference to the accompanying drawings. FIG. 1 represents the first embodiment of the present invention. Specifically, the apparatus for determination according with the present invention basically comprises a reagent layer 1 and a spreading layer 2 disposed contiguously to the reagent layer 1. The reagent layer 1, when necessary, may have a supporting member 3 attached thereto through the medium of a double-faced adhesive tape 4 or an adhesive agent layer (not shown).

The reagent layer has no particular restriction except for the sole requirement that it should have a pigment deposited thereon and should be permeable to water. Generally, the pigment is either directly deposited on a carrier or preparatorily adsorbed on minute particles and then dispersed and deposited on a carrier. In this case, when the pigment is deposited in conjunction with a water-soluble polymeric material as a binder, the pigment is uniformly dispersed and stably deposited. The pigment thus dispersed and deposited is readily dissolved out when the reagent layer is exposed to an aqueous solution at the time of use.

The carriers which are effectively used herein include water-permeable carriers such as filter paper, woven fabric, non-woven fabric, and knit fabric, for example. The water-soluble polymeric materials which are effectively usable as a binder herein include polyvinyl pyrrolidone, polyvinyl alcohol, hydroxypropyl cellulose, and gelatin, for example. These water-soluble polymeric materials are used either singly or in the form of a combination of two or more members.

The minute particles have no particular restriction except for the sole requirement that they should be capable of adsorbing the pigment. The average particle diameter of these minute particles is preferably in the range of 10 to 400 $\mu$m, preferably 50 to 150 $\mu$m. The minute particles which are usable effectively herein include those of sellaite, silica gel, polyamide, and alumina, for example. They are used either singly or in the form of a combination of two or more members.

The spreading layer is formed of an absorbent substance possessing a suitable thickness and a specific water-filtering time. The absorbent substances which are usable effectively herein include filter paper, woven fabric, non-woven fabric, and knit fabric, for example. When the spreading layer incorporates therein a surfactant or a wetting agent, it may be enabled to acquire a desirable ability to assume color.

The surfactants and the wetting agents which are usable effectively herein include anionic surfactants such as alkyl sulfates, alkylbenzene sulfonates, succinic dialkyl ester sodium sulfonates, amide sulfonates, sulfuric sodium esters of ricinolates, $\alpha$-sulfo-fatty acid alkyl ester salts, monosodium-$\alpha$-sulfono-fatty acid esters, and sodium dialkyl phosphates and nonionic surfactants such as polyoxyethylene alkyl phenols, polyoxyethylene-polyoxypropylene-polyoxyethylene glycol, polyoxyethylene-9, 10-octadecane diol, polyoxyethylene-9, 10-dihydroxystearonitrile, and ethylene oxide adducts of linear dihydric alcohols, for example.

In the production of the apparatus for determination according with the present invention, the reagent layer which has dispersed in a binder either the pigment or the minute particles having the pigment adsorbed thereon is obtained by preparing a binder-containing solvent having the pigment dissolved or suspended therein, applying the solvent on a carrier by the use of a coating machine or a spray gun, and causing the solvent to impregnate the carrier. By superposing a spreading layer, when necessary, through the medium of an adhesive agent on the reagent layer obtained as described above, the apparatus for determination according with the present invention is produced. Optionally, a supporting member may be attached to the reagent layer with the aid of a double-faced adhesive tape or an adhesive agent.

It is otherwise permissible to effect integral formation of the reagent layer and the spreading layer by evenly applying on one surface of the spreading layer, when necessary, treated in advance with a surfactant or a wetting agent the binder-containing solvent having the pigment dissolved or suspended therein thereby causing the applied solvent to impregnate partially the combined layers except for the spreading layer.

Figure 2:
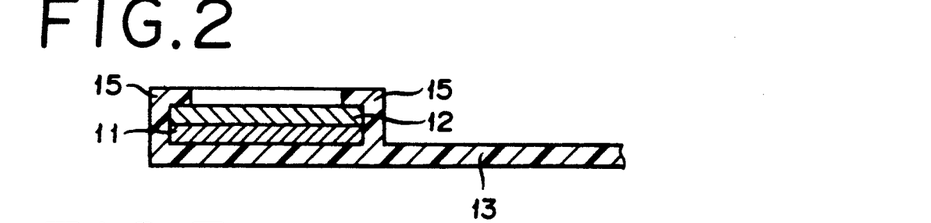
Figure 3:
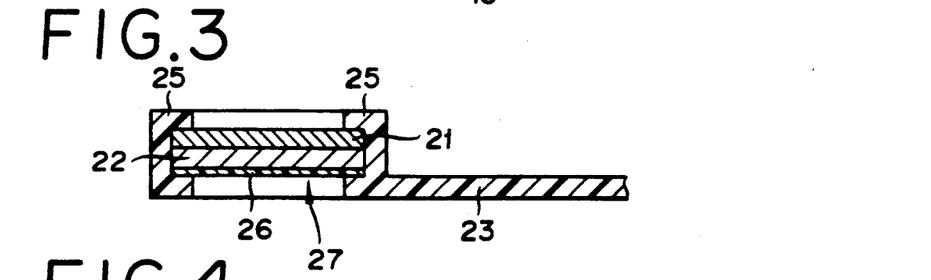

FIG. 2 represents the second embodiment of the present invention, which is produced by integrally forming a reagent layer 11 and a spreading layer 12 and fixing them on a supporting member 13 which is provided with a retaining part 15. FIG. 3 represents the third embodiment of the present invention, which is produced by integrally forming a reagent layer 21 and a spreading layer 22 and fixing them through the medium of a transparent film 26 on a supporting member 23 which is provided with a retaining part 25 and an opening part 27.

When the apparatus for determination according with the present invention is immersed in a solution subjected to determination, the aforementioned pigment is dissociated into ions as indicated by the formula I or II and the color consequently assumed is manifested in the spreading layer with the density of the color varied proportionately to the degree of dissociation. The determination of the color is accomplished, therefore, by projecting a light of a specific wavelength on the spreading layer and measuring the reflection absorbance. Otherwise, this determination may be attained by comparing the color so manifested with the table of standard color densities. In the case of the apparatus for determination shown in FIG. 3, when a solution subjected to determination such as, for example, blood, is dropped onto the reagent layer 21, the blood cells in the blood are filtered out by the reagent layer 21 and the blood plasma component of the blood is mainly passed through the reagent layer 21 and allowed to reach the spreading layer 22. In the meantime, the pigment is dissociated and the color produced in the spreading layer 22 has the density thereof varied proportionately to the ion concentration. By projecting a light upwardly through the opening part 27 on the lower side and measuring the resultant reflection absorbance, the density of the color can be determined without being affected by the coloring component inherently present in a colored solution such as the blood.

Figure 4:
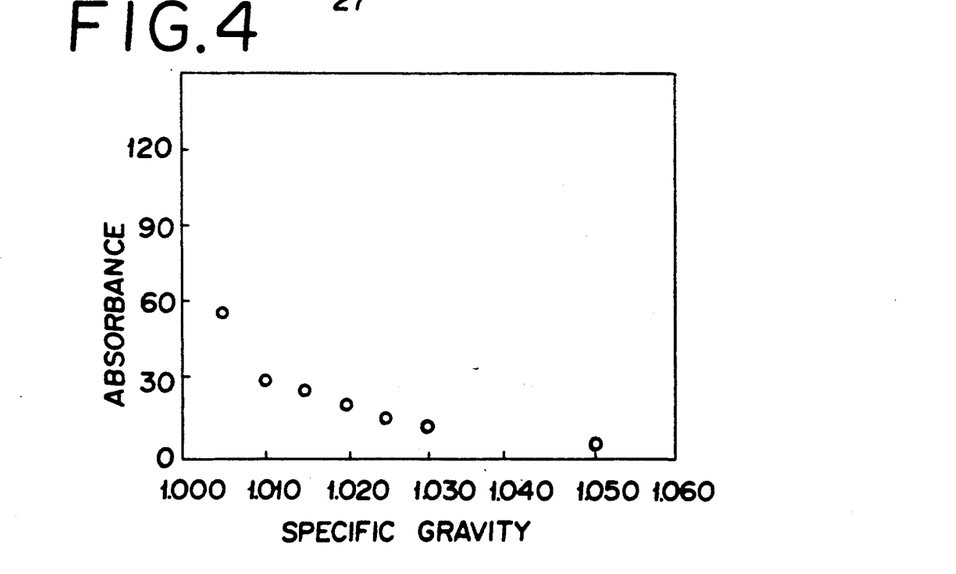
FIGS. 4 to 6 are graphs each showing the relation between the absorbance and the specific gravity of a varying pigment.
Figure 5:
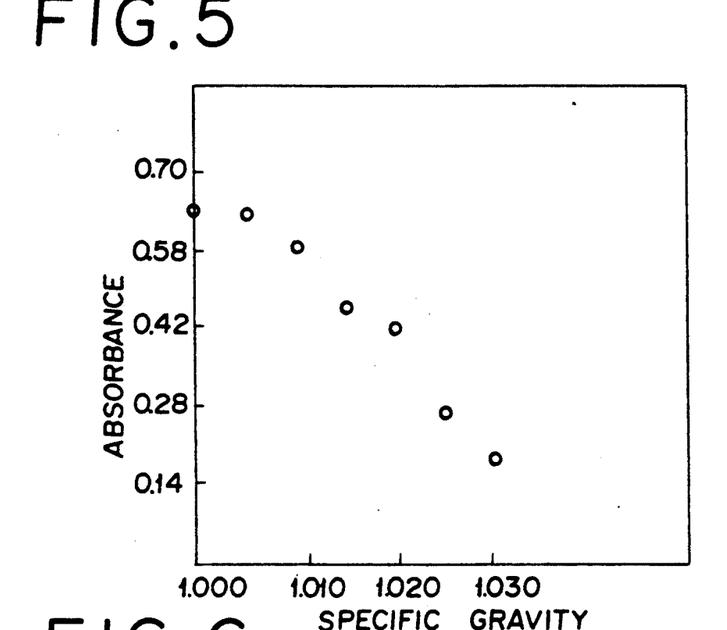
Figure 6:
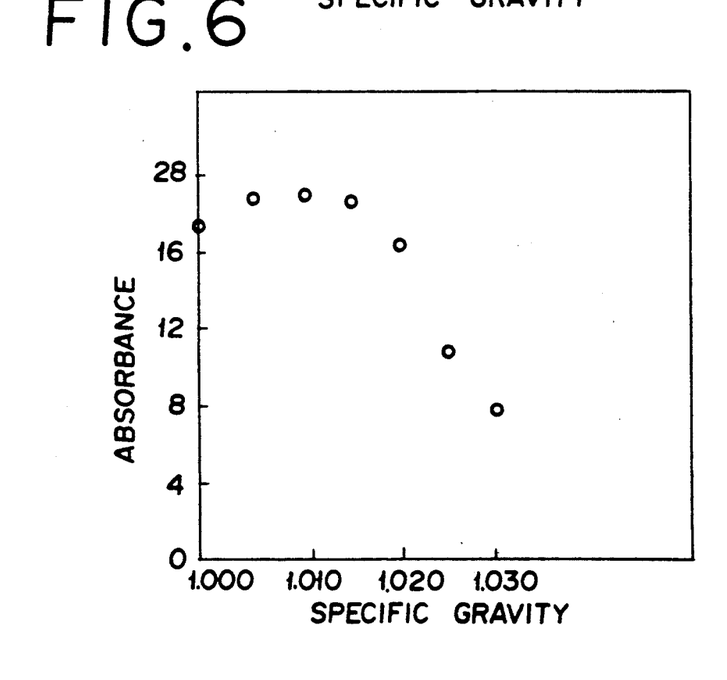

FIG. 4 represents a solubility curve of indigo carmine, FIG. 5 represents a solubility curve of basic blue-3, and FIG. 6 represents a solubility curve of basic red-29, respectively.

Since the absorbance of this sort, as clearly demonstrated in the working examples cite hereinafter, is correlated with the concentration and specific gravity of the solution subjected to determination, the concentration and specific gravity can be determined by measuring the absorbance. Further, since the absorbance is correlated with the ion concentration, namely the osmotic pressure, the osmotic pressure can be determined by measuring the absorbance. Alternatively, this detection may be accomplished by colorimetry.

Now, the present invention will be described more specifically below with reference to working examples.

EXAMPLE 1

Figure 7:
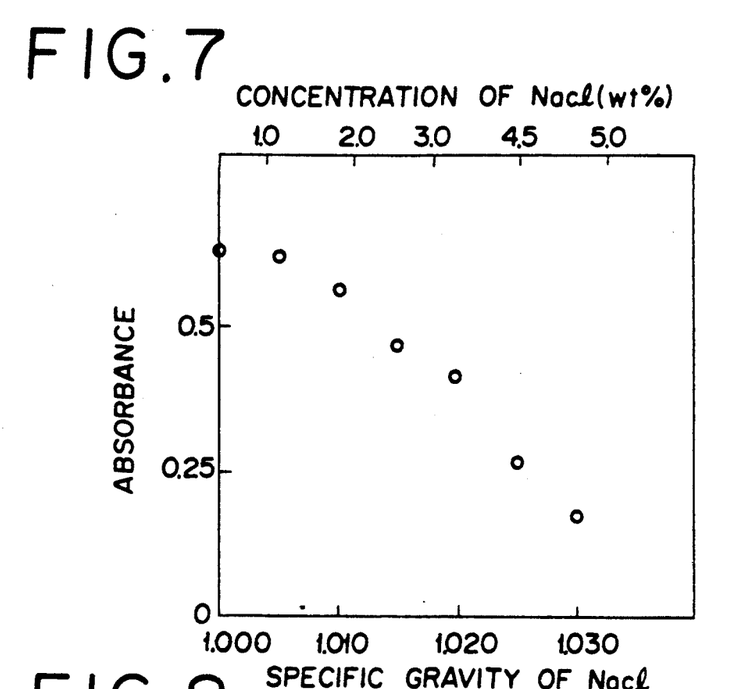
FIG. 7 is a graph showing the relation between the absorbance, specific gravity, and ion concentration of a solution.

To determine the ion concentration and specific gravity of an aqueous sodium chloride solution, 1 ml of the aqueous solution and a pigment (indigo carmine) added thereto in an amount slightly exceeding saturated concentration were stirred for solution of the pigment. A portion of the supernatant of the resultant solution was withdrawn in a syringe provided with a membrane filter, diluted to 100 times the original amount, and tested for absorbance. The measurement of the absorbance was made with a spectrophotometer (produced by Hitachi, Ltd. and marketed under product code of "U-2000"). The relation between the absorbance, sodium chloride concentration, and specific gravity of the aqueous sodium chloride solution is shown in FIG. 7. It is clearly noted from the graph that the absorbance varied proportionately to the ion concentration of the solution. The calibration curve obtained by the test described above can be utilized for determining the ion concentration of a given sample of unknown ion concentration. When the test was repeated by following the procedure described above, excepting basic blue 3 and basic red 29 were each used as a pigment in the place of indigo carmine, similar results were obtained.

EXAMPLE 2

Figure 8:
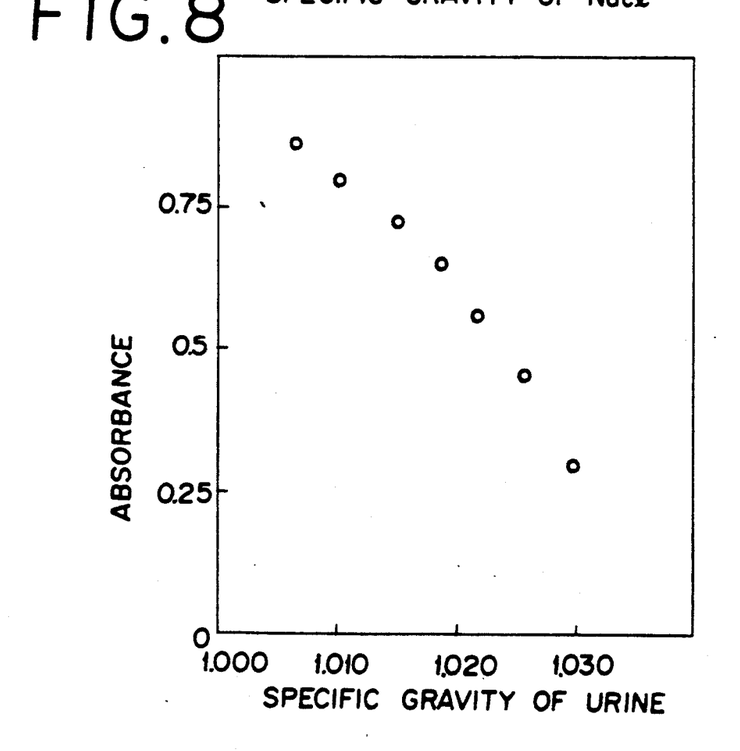
FIGS. 8 to 10 are graphs each showing the relation between the absorbance and the specific gravity of urine.

Real urine was analyzed severally by the method of the present invention and by the use of a refraction type urine hydrometer (produced by Nippon Kogaku K.K. and marketed under trademark designation of "Uripet") and the results were compared. The test was performed by a procedure which comprised stirring 1 ml of the urine and 1 $\mu$l of indigo carmine added thereto for 1 minute, removing 1 $\mu$l of the supernatant of the resultant solution, diluting the removed supernatant with 1 ml of distilled water, and measuring the absorbance of the diluted supernatant in the same manner as in Example 1. The results are shown in FIG. 8.

EXAMPLE 3

Figure 9:
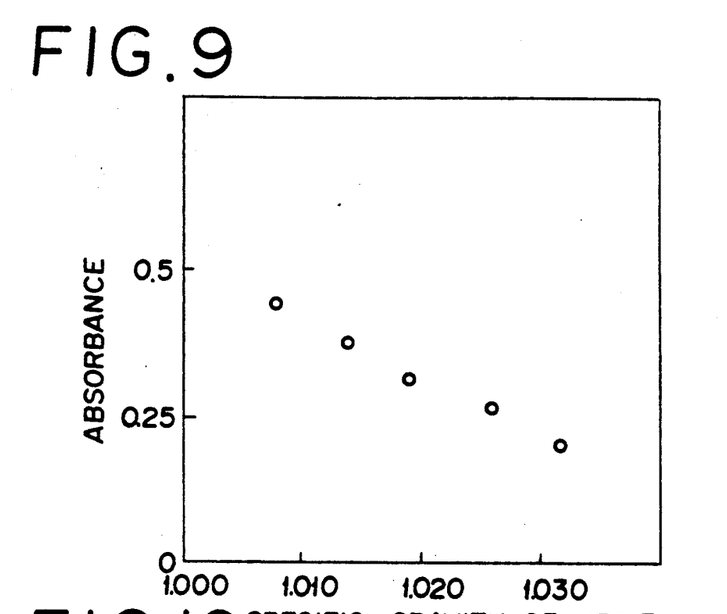

The same solution (urine) subjected to determination as used in Example 2 was analyzed in a system using a coloring substance formed of a precursor of pigment and a developer. The test was performed by a procedure which comprised stirring 1 ml of the urine and 5 mg of N,N-dimethyl aniline added thereto for 1 minute, stirring the supernatant of the resultant solution and 10 $\mu$l of an aqueous 0.5% fast blue B salt solution added thereto, and measuring the absorbance of the stirred mixture. The results are shown in FIG. 9.

EXAMPLE 4

Figure 10:
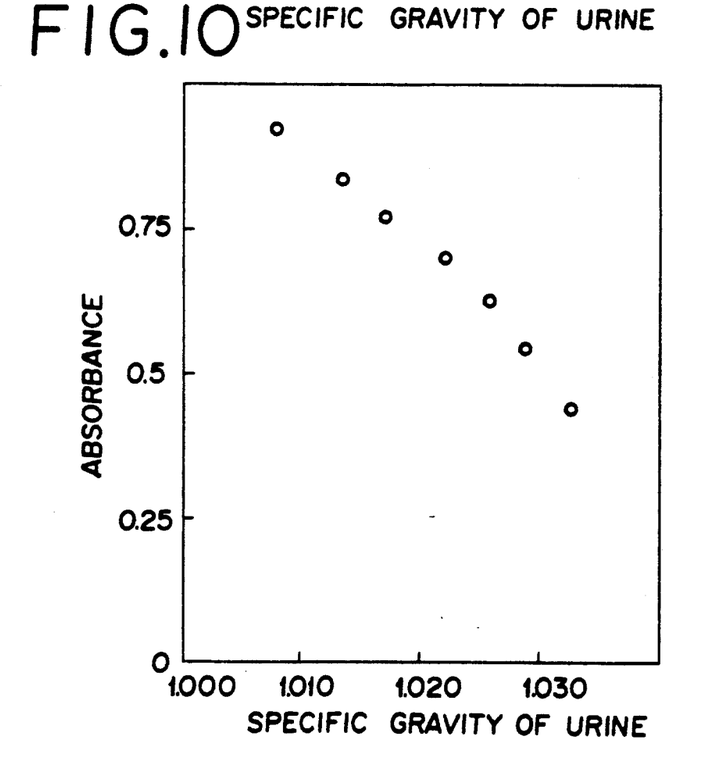

The test of urine was repeated by following the procedure of Example 2, except that a prescribed amount of salt was added to the urine in advance of the test. The test was performed by a procedure which comprised dissolving 10 mg of sodium chloride in 1 ml of urine, stirring the resultant urine solution of salt and 10 mg of indigo carmine added thereto for 1 minutes, removing 10 ul of the supernatant of the stirred solution, diluting the removed supernatant with 1 ml of distilled water, and measuring the absorbance of the diluted supernatant. The results are shown in FIG. 10. It is clearly noted from the graph that the absorbance was shifted in proportion to the amount of added ion. The data indicate that the range of absorbance to be determined could be controlled by the addition of a prescribed amount of the salt to the solution subjected to determination. Where the range of absorbance to be determined was fixed, the range of ion concentration to be determined could be controlled by the addition of the salt.

EXAMPLE 5

Figure 11:
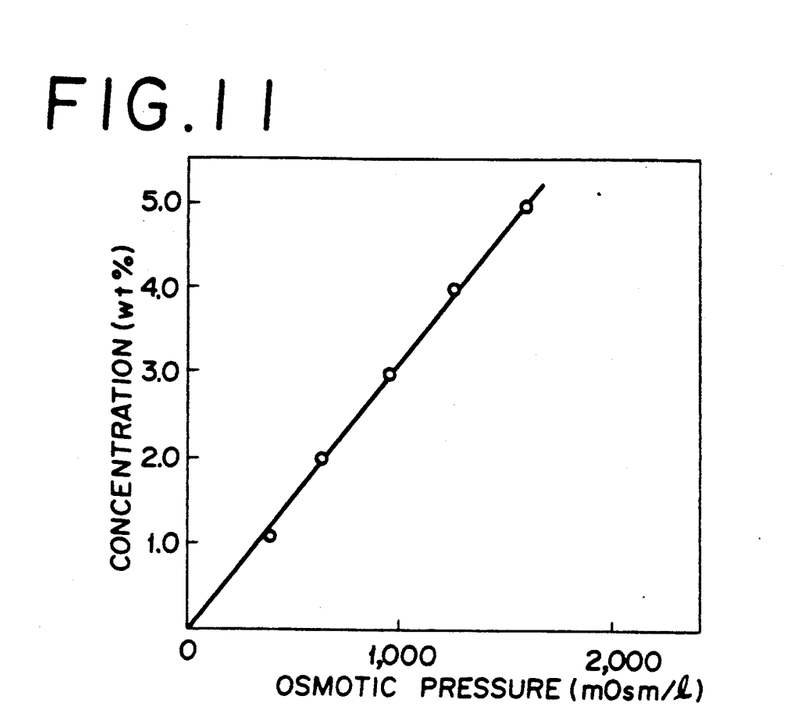
FIG. 11 is a graph showing the relation between the ion concentration and the osmotic pressure of a solution.
Figure 12:
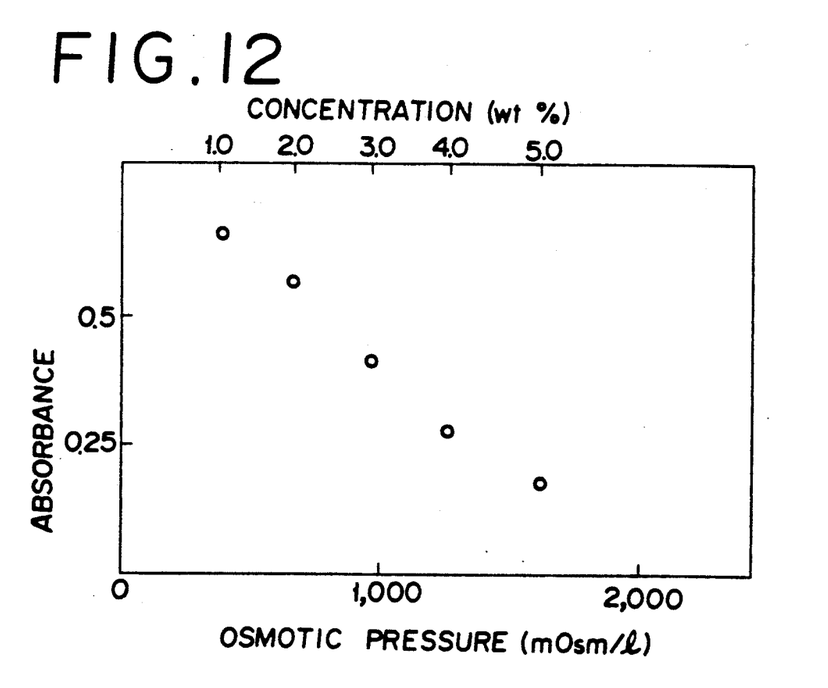
FIG. 12 is a graph showing the relation between the ion concentration, absorbance, and osmotic pressure of a solution.

To determine the ion concentration and osmotic pressure of an aqueous sodium chloride solution, 1 ml of the solution and a pigment (indigo carmine) added thereto in an amount slightly exceeding saturated concentration were stirred for solution of the pigment. A portion of the supernatant of the resultant solution was withdrawn in a syringe provided with a membrane filter and tested for osmotic pressure. The measurement of the osmotic pressure was made with an osmometer (produced by Advanced Instruments Corp. and marketed under trademark designation of "Advanced Cryomatic, Model 3C2"). The relation between the sodium chloride concentration and the osmotic pressure of the aqueous sodium chloride solution is shown in FIG. 11. It is clearly noted from the graph that the osmotic pressure varied proportionately to the ion concentration in the solution. The relation between the ion concentration of the aqueous sodium chloride solution and the absorbance and osmotic pressure, found on the basis of the data of FIG. 7 obtained in Example 1 concerning the relation between the absorbance and the sodium chloride concentration and the data of FIG. 11 obtained in the present example concerning the relation between the sodium chloride concentration and the osmotic pressure, is shown in FIG. 12. The calibration curve obtained by the test described above can be utilized for determining the osmotic pressure of a sample solution of unknown osmotic pressure.

In the test preformed by following the procedure described above, excepting basic blue 3 and basic red 29 were each used as a pigment in the place of indigo carmine, similar results were obtained.

EXAMPLE 6

A filter paper (Advantic No. 202) was immersed in and impregnated with ethanol containing 0.5% of a nonionic surfactant of alkylallyl polyether alcohol (produced by Rhom and Haas Company and marketed under trademark designation of "Triton X-100"), dried at 60° C. for 30 minutes, and used as a spreading layer.

Separately, a filter paper (Advantic No. 462) was immersed in and impregnated with an aqueous 4% indigo carmine solution, dried at 60° C. for 30 minutes, cut in a suitable size, and used as a reagent layer. A testing device was obtained by enclosing the reagent layer and the spreading layer with a holder.

EXAMPLE 7

A reagent layer was formed on the reverse side of the spreading layer obtained in the same manner as in Example 6, by spraying on the surface a pigment suspension formed of chloroform containing 2% of indigo carmine and 2% of polyvinyl pyrrolidone K-3000 and drying the applied layer of the suspension at room temperature for 30 minutes. A testing device was obtained by cutting in a suitable size the spreading layer having the reagent layer superposed thereon as described above and applying the cut composite fast to one end of a supporting member of polystyrene film through the medium of a double-faced adhesive tape.

EXAMPLE 8

A reagent layer was formed by spraying on a double-faced adhesive tape a pigment suspension formed of chloroform containing 2% of indigo carmine and 2% of polyvinyl pyrrolidone K-300 and then drying the applied layer of the suspension at room temperature for 30 minutes. The reagent layer side of the double-faced adhesive tape was attached fast to a spreading layer produced separately in the same manner as in Example 6. A testing device was obtained by cutting the resultant composite in a suitable size and attaching the cut piece of composite to one end of a supporting member of polystyrene film.

EXAMPLE 9

A reagent layer was formed by spraying on a double-faced adhesive tape a pigment solution formed of methanol containing 2% of indigo carmine and 2% of polyvinyl pyrrolidone K-3000 and drying the applied layer of the pigment solution at room temperature for 30 minutes. The reagent layer side of the double-faced adhesive tape was attached fast to a spreading layer separately obtained in the same manner as in Example 6. A testing device was obtained by cutting the resultant composite in a suitable size and attaching the cut piece of composite to one end of a supporting member.

EXAMPLE 10

Pigment-adsorbed minute particles were prepared by stirring 3 g of sellaite in 3 ml of an aqueous 3% indigo carmine solution for 8 hours, filtering the resultant mixture, and drying the residue of filtration by a desiccator. On a spreading layer separately obtained in the same manner as in Example 1, a reagent layer was deposited by preparing a pigment-absorbed particle suspension formed of chloroform containing 2% of the pigment-adsorbed minute particles and 2% of polyvinyl pyrrolidone K-3000, spraying the suspension on the reverse side of the spreading layer, and drying the applied layer of the suspension at room temperature for 30 minutes. A testing device was obtained by cutting in a suitable size the resultant composite having the reagent layer superposed on the spreading layer and attaching fast the cut piece of the composite to one end of a supporting member of polystyrene film through the medium of a double-faced adhesive tape.

EXAMPLE 11

A spreading layer was produced by causing non-woven fabric (Selen SK-706) to be immersed in and impregnated with ethanol containing 0.5% of Triton X-100 and drying the wet non-woven fabric at 60° C. for 30 minutes. Then, on the spreading layer, a reagent layer was formed by preparing a pigment suspension formed of chloroform containing 2% of indigo carmine and 2% of polyvinyl pyrrolidone K-3000, spraying the suspension on the reverse side of the spreading layer, and drying the applied layer of the suspension at room temperature for 30 minutes. A testing device was obtained by cutting in a suitable size the resultant composite having the reagent layer superposed on the spreading layer and attaching fast the cut piece of composite to one end of a supporting member of polyethylene film through the medium of a double-faced adhesive tape.

Evaluation of Testing Device

Figure 13:
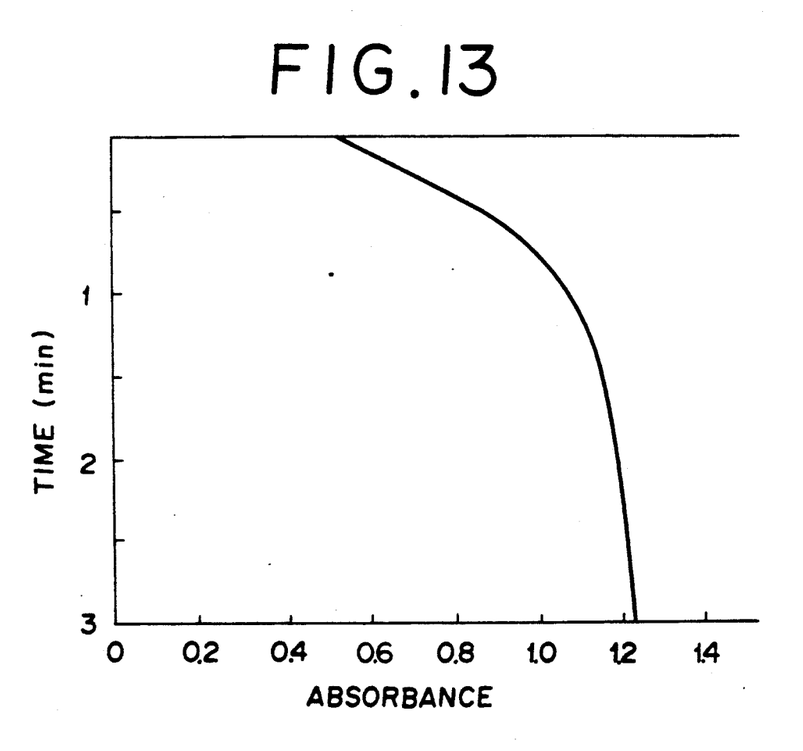
FIG. 13 is a graph showing the change of absorbance of reflection on the surface of a spreading layer.

The obverse side of the spreading layer obtained in Example 7 was wetted with dropping water (standard solution of specific gravity of 1.000). On elapse of 3 minutes after the wetting, the reflection absorbance on the obverse side of the spreading layer at a wavelength of 608 nm was measured along the course of time. The relation between the variation in the reflection absorbance and the time of standing is shown in FIG. 13. The measurement of the reflection absorbance was made by the use of an instrument produced by Otsuka Denshi K.K. and marketed under product code of "MCPD-200."

EXAMPLE 12

In each of the testing devices produced in Examples 6 to 11, an aqueous sodium chloride solution having a varying specific gravity in the range of 1.000 to 1.030 was dropped onto the obverse side of the spreading layer and, on elapse of one minute following the wetting, the reflection absorbance at 603 nm of the obverse side was measured. The results are shown in Table 1.

It is clearly noted from Table 1 that the colors produced were severally correlated with relevant specific gravities. The same correlation between the specific gravity and the coloration was obtained when the test was repeated by the procedure described above, excepting basic blue 3 and basic red 29 were each used instead.

TABLE 1

| Specific gravity | 0.000 | 1.005 | 1.010 | 1.015 | 1.020 | 1.025 | 1.030 |
|---|---|---|---|---|---|---|---|
| % by weight | 0.000 | 1.142 | 1.842 | 2.542 | 3.242 | 3.942 | 4.642 |
| Example 6 | 0.71 | 0.54 | 0.50 | 0.44 | 0.32 | 0.24 | 0.14 |
| Example 7 | 0.96 | 0.73 | 0.62 | 0.48 | 0.42 | 0.34 | 0.26 |
| Example 8 | 0.94 | 0.73 | 0.63 | 0.51 | 0.44 | 0.37 | 0.29 |
| Example 9 | 0.97 | 0.80 | 0.71 | 0.62 | 0.55 | 0.46 | 0.40 |
| Example 10 | 0.55 | 0.48 | 0.42 | 0.37 | 0.31 | 0.26 | 0.20 |
| Example 11 | 0.96 | 0.84 | 0.73 | 0.61 | 0.52 | 0.44 | 0.37 |

What is claimed is:

1. An apparatus for determining an ion concentration, specific gravity or osmotic pressure of a liquid test sample, said apparatus comprising:
   a reagent layer having a pigment which has a given property in which the solubility of said pigment varies in accordance with ion concentration in said liquid test sample; and
   a spreading layer disposed contiguously to said reagent layer so that the amount of said pigment dissolved out of said reagent layer into said spreading layer varies in accordance with the ion concentration in said liquid test sample;
   wherein the ion concentration is indicated by a color developed on a surface of said spreading layer.

2. An apparatus according to claim 1, wherein said pigment is a water-soluble pigment possessing an ionically functional group.

3. An apparatus according to claim 1, wherein said reagent layer comprises a water-permeable carrier and said pigment deposited thereon.

4. An apparatus according to claim 3, wherein said carrier is a filter paper or a cloth.

5. An apparatus according to claim 3 or claim 4, wherein said pigment is adsorptively dispersed on said carrier with a polymeric material, or said pigment is adsorbed on minute particles which are adsorptively dispersed on said carrier with a polymeric material.

6. An apparatus according to claim 5, wherein said polymeric material is at least one member selected from the group consisting of polyvinyl pyrrolidone, polyvinyl alcohol, hydroxypropyl cellulose, and gelatin.

7. An apparatus according to claim 5, wherein said minute particles are selected from the group consisting of sellaite, silica gel, polyamide and alumina.

8. An apparatus according to claim 1, wherein said spreading layer is filter paper or a cloth.

9. An apparatus according to claim 8, wherein said spreading layer contains a surfactant or a wetting agent.

10. An apparatus according to claim 1, wherein said spreading layer contains a salt to be used for the adjustment of the range of ion concentration in said liquid test sample.

11. An apparatus according to claim 1, wherein said reagent layer and said developer spreading layer are deposited on a supporting member.

12. An apparatus according to claim 2, wherein said reagent layer and said spreading layer are deposited on a supporting member.

13. An apparatus according to claim 3, wherein said reagent layer and said spreading layer are deposited on a supporting member.

14. An apparatus according to claim 4, wherein said reagent layer and said spreading layer are deposited on a supporting member.

15. An apparatus according to claim 5, wherein said reagent layer and said spreading layer are deposited on a supporting member.

16. An apparatus according to claim 6, wherein said reagent layer and said spreading layer are deposited on a supporting member.

17. An apparatus according to claim 7, wherein said reagent layer and said spreading layer are deposited on a supporting member.

18. An apparatus according to claim 8, wherein said reagent layer and said spreading layer are deposited on a supporting member.

19. An apparatus according to claim 9, wherein said reagent layer and said spreading layer are deposited on a supporting member.

20. An apparatus according to claim 10, wherein said reagent layer and said spreading layer are deposited on a supporting member.

21. An apparatus according to claim 1, wherein said pigment is selected from the group consisting of indigo carmine, basic blue and basic red.

* * * * *

UNITED STATES PATENT AND TRADEMARK OFFICE
CERTIFICATE OF CORRECTION

PATENT NO. : 5,215,712
DATED : June 1, 1993
INVENTOR(S) : Tetsuro KAWANISHI et al It is certified that error appears in the above-indentified patent and that said Letters Patent is hereby corrected as shown below:

In Column 10, line 14, delete "preformed" and insert -- performed --.

In Column 12, line 28, following ";", insert -- and --.

In Column 12, line 61, delete "developer".

Signed and Sealed this

Eleventh Day of January, 1994

*Attest:*

BRUCE LEHMAN

*Attesting Officer*  *Commissioner of Patents and Trademarks*